United States Patent [19]
Matier et al.

[11] Patent Number: 4,849,515
[45] Date of Patent: Jul. 18, 1989

[54] CLINDAMYCIN-2-PHOSPHORYL BENZYLATE

[75] Inventors: William L. Matier, Hockessin, Del.; Chi Woo; Ying-Chi Lee, both of Libertyville, Ill.

[73] Assignee: E. I. du Pont de Nemours and Company, Wilmington, Del.

[21] Appl. No.: 234,717

[22] Filed: Aug. 22, 1988

[51] Int. Cl.$^4$ ............................................. C07H 11/04
[52] U.S. Cl. .................................. 536/16.5; 536/16.2
[58] Field of Search ....................... 536/16.5, 22, 16.2, 536/29

[56] References Cited

U.S. PATENT DOCUMENTS 3,487,068 12/1969 Morozowich et al. ............. 260/210
3,892,729 7/1975 Birkenmeyer .................. 260/210 R
4,742,163 5/1988 Ogata .................................... 536/29

Primary Examiner—Joseph L. Schofer
Assistant Examiner—Gary Kung
Attorney, Agent, or Firm—Gildo E. Fato

[57] ABSTRACT

A novel compound, also known as 7(s)-chloro-7-deoxylincomycin-2-phosphoryl benzylate, useful an an intermediate in the production of the antibiotic, clindamycin-2-phosphate.

1 Claim, No Drawings

CLINDAMYCIN-2-PHOSPHORYL BENZYLATE

BACKGROUND OF THE INVENTION

Clindamycin, 7(S)-chloro-7-deoxylincomycin, the preparation of which is described in U.S. Pat. No. 3,487,068 issued Dec. 30, 1969, is a potent antibacterial agent. Clindamycin is a derivative of the amino acid trans-L-4-n-propylhygrinic acid, attached to a sulfur-containing derivative of an octose.

Clindamycin and lincomycin bind exclusive to the 50 S subunit of bacterial ribosomes and suppress protein synthesis. Although clindamycin, erythromycin and chloramphenicol are not structurally related, they all act at this site, and the binding of one of these antibiotics to the ribosome may inhibit the reaction of the other. In general, clindamycin is similar to erythromycin in its activity in vitro against pneumococci, *Strep. pyogenes,* and viridans streptococci. Almost all such bacterial strains are inhibited by concentrations of 0.04 μg/mL. It is also active against many strains of Staph. aureus but may not inhibit methicillin-resistant strains. Clindamycin is nearly completely absorbed following oral administration, and peak plasma concentrations of 2 to 3 μg/mL are attained within 1 hour after the injestion of 150 mg. The presence of food in the stomach does not reduce absorption significantly. The half-life of the antibiotic is about 2.5 hours, and modest accumulation of drug is to be expected if it is given at 6 hour intervals. The phosphate ester of clindamycin which is given parenterally, is also rapidly hydrolyzed in vivo to the active parent compound. Following intramuscular injection, peak concentrations in plasma are not attained for 3 hours in adults and 1 hour in children. The recommended parenteral dosages provide peak plasma concentrations of 5 to 15 μg/mL and effective antimicrobial activity for approximately 8 hours. Most of the drug is inactivated by metabolism to N-demethylclindamycin and clindamycin sulfoxide, which are excreted in the urine and bile. The half-life of clindamycin is lengthened only slightly in patients with markedly impaired renal function, and little adjustment of dosage is required for such individuals.

DETAILED DESCRIPTION OF THE INVENTION

In accordance with one embodiment of the present invention, clindamycin phosphate is prepared by first preparing the novel clindamycin phosphoryl benzylate. Preparation of clindamycin phosphate by means of this intermediate, which can be easily isolated and purified, eliminates the need for use of column chromatography. For example, see U.S. Pat. No. 3,487,068 issued Dec. 30, 1969, particularly Examples 1 and 2 wherein lincomycin-2-phosphate and 7(S)-chloro-7-deoxylincomycin-2-phosphate are purified by column chromatography. In a specific embodiment of the invention, this monophosphate benzyl ester is prepared by treating protected clindamycin hydrochloride with phosphorous oxychloride in the presence of a suitable solvent to obtain a reaction mixture, adding benzyl alcohol to the reaction mixture and subsequently adding water to complete the reaction. In this reaction, the benzyl alcohol is not only a reactant but also a powerful solvent in which the desirable intermediate is freely soluble. Moreover, any by-products are easily removed by washing with an aqueous solution.

The overall process of the invention can be depicted by the following reaction scheme.

Reaction Sequence

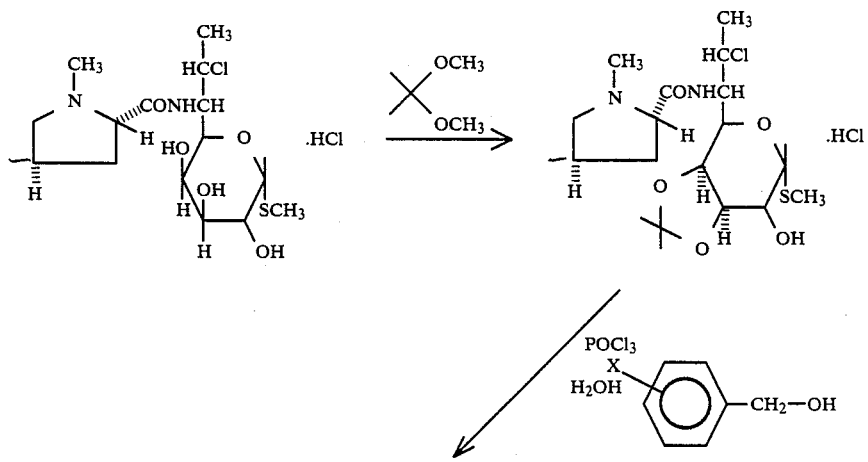

-continued
Reaction Sequence

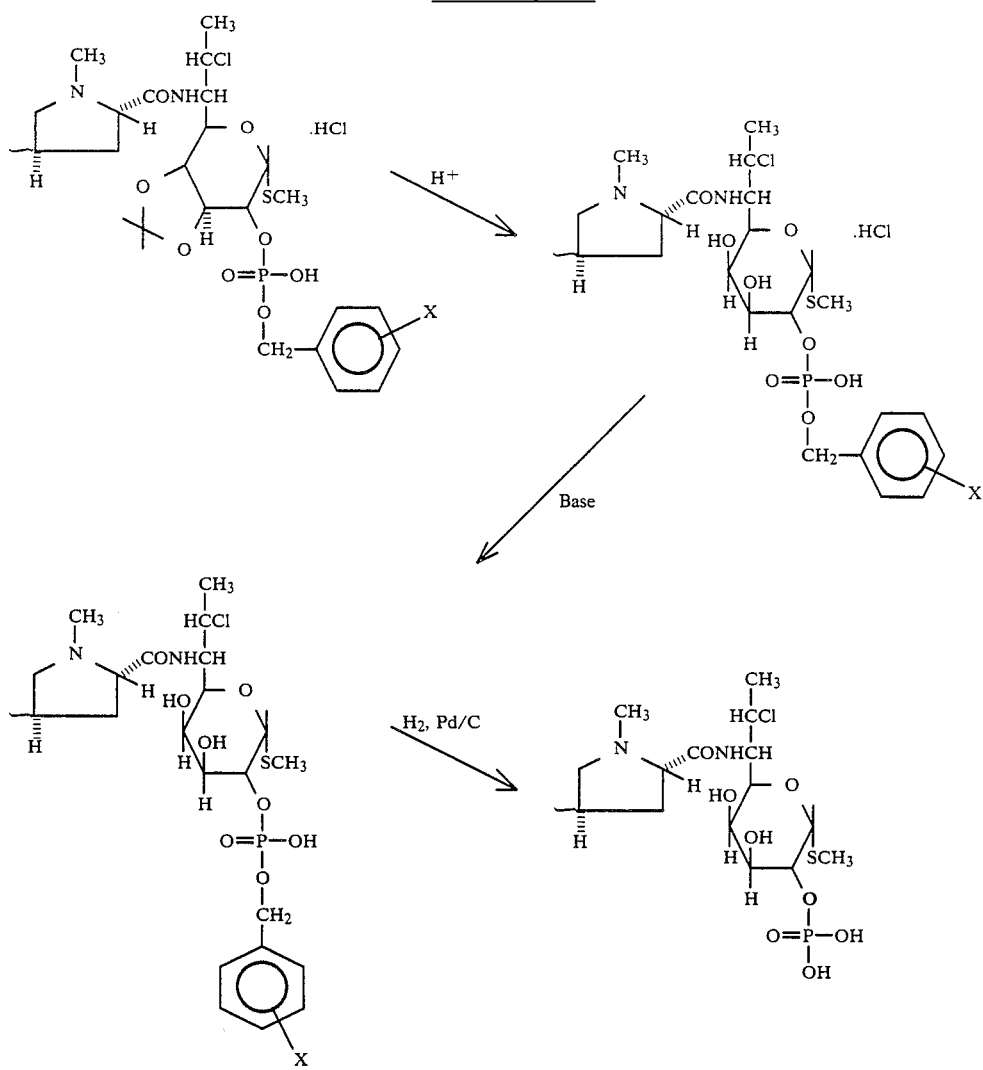

X = H, loweralkyl, halo, loweralkoxy, —NO$_2$, —CF$_3$, or phenyl

EXAMPLE 1

Synthesis of Clindamycin HCL

Summary of process

Hexachloroethane (306 g) (Note) is suspended in 1,2-dichloroethane (100 mL) and the suspension is cooled. Triphenylphosphine (312 g) dissolved in 1,2-dichloroethane (500 mL) is added slowly and stirring is continued to ensure complete formation of the Rydon reagent.

DMF (100 mL) is then added and the resulting yellow solution is stirred for 1 hour before the addition of lincomycin HCl (100 g). The mixture is heated and agitated for several hours, cooled and hydrolyzed. A series of acid/base extractions is then employed to remove the by-product triphenylphosphine oxide. Clindamycin HCl (73–78 g; 70–75%) is finaly crystallized from ethanol. Melting point: 132° to 133° C.

NOTE: Hexachloroethane is used as the source of chlorine to form the Rydon reagent, triphenylphosphinedichloride.

EXAMPLE 2

Clindamycin Phosphate

General description of manufacturing method

STEP I: Preparation of protected clindamycin hydrochloride.

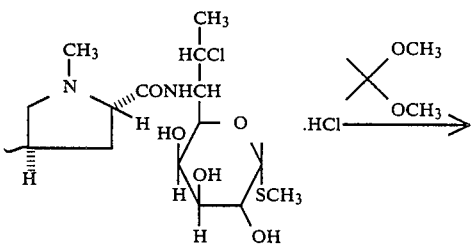

-continued

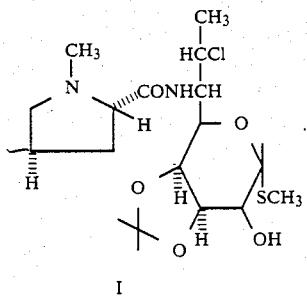

Clindamycin hydrochloride is heated with 2,2-dimethoxypropane in a suitable solvent. Upon cooling, the protected clindamycin hydrochloride, I, is isolated by filtration. Melting point: 16220 to 163° C.

EXAMPLE 3

STEP II: Preparation of protected clindamycin benzylate hydrochloride.

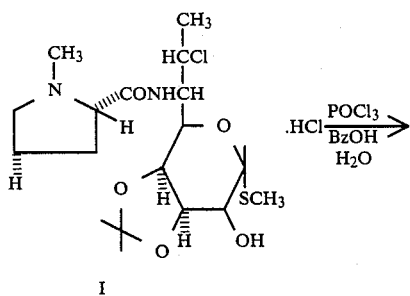

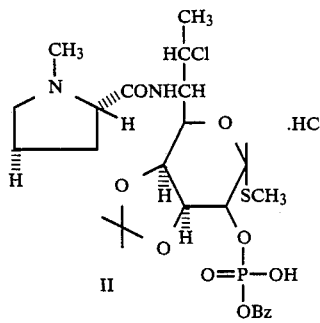

The protected clindamycin hydrochloride, I, is treated with phosphorous oxychloride in a suitable solvent, such as pyridine, at sub-ambient temperatures. Benzyl alcohol is added slowly then the reaction mixture is allowed to warm to room temperature. Water is then added slowly, and the reaction mixture is stirred for a period of time at room temperature. After separation of the aqueous layer, the organic layer is washed and dried; crystallization of the product is affected by the addition of a suitable solvent, such as acetone, to the organic layer. The protected clindamycin hydrochloride, II, is isolated by filtration. Melting point: 254° to 258° C.

EXAMPLE 4

STEP III: Preparation of deprotected clindamycin benzylate hydrochloride.

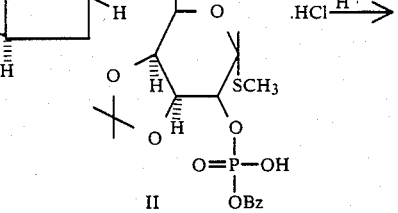

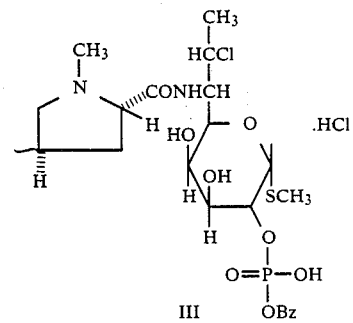

The protected clindamycin benzylate hydrochloride, II, is heated with acid (i.e. aqueous hydrochloride acid) in a suitable solvent such as methanol. Water is added slowly to precipitate the product then a portion of the solvent distilled off. Upon cooling the deprotected clindamycin benzylate hydrochloride, III, is isolated by filtration.

EXAMPLE 5

STEP IV: Preparation of clindamycin benzylate free base.

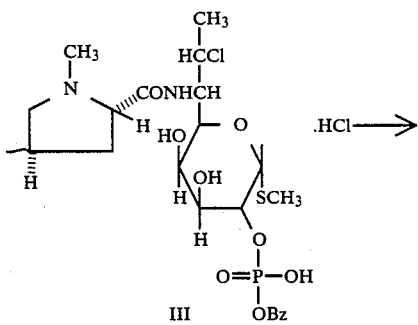

Deprotected clindamycin benzylate hydrochloride, III, is treated with a suitable base such as ammonium hydroxide in water. Neutralization of the solution with a suitable acid (i.e. aqueous hydrochloric acid) precipitates clindamycin benzylate free base, IV, which is isolated by filtration. Melting point: 218° to 220° C.

EXAMPLE 6

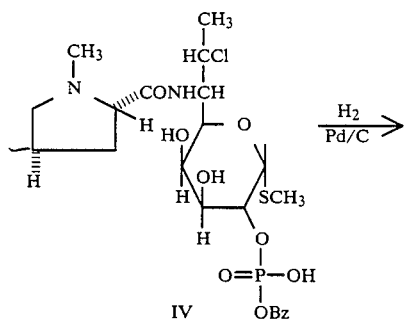

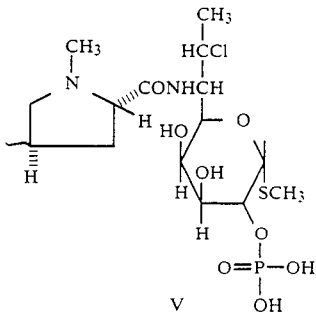

STEP V: Preparation of clindamycin phosphate.

Treatment of clindamycin benzylate free base, IV, with hydrogen gas in the presence of Pd/C catalyst in a suitable solvent (i.e. methanol, water or a methanol/water mixture) gives clindamycin phosphate, V. Following the completion of the hydrogenolysis, the water/methanol solvent ratio may be adjusted and a portion of a suitable co-solvent such as acetonitrile may be added. The reaction mixture is heated to ensure dissolution of product, then filtered to remove the catalyst. Additional acetonitrile is added to the filtrate, which is then cooled, to effect crystallization of the product. The clindamycin phosphate, V, is isolated by filtration.

If required, this material may be purified by recrystallization, following charcoal treatment if necessary, from a suitable solvent system (i.e. water, methanol, acetonitrile or a mixture of these solvents). Melting point: 208° to 212° C.

What is claimed is:

1. The compound 7(S)-chloro-7-deoxylincomycin-2-phosphoryl benzylate.

* * * * *